United States Patent [19]

Schroeppel

[11] Patent Number: 5,174,303
[45] Date of Patent: Dec. 29, 1992

[54] PACER LEAD WITH REPLACEABLE SENSOR

[75] Inventor: Edward A. Schroeppel, Lake Jackson, Tex.

[73] Assignee: Intermedics, Inc., Angleton, Tex.

[21] Appl. No.: 695,569

[22] Filed: May 3, 1991

[51] Int. Cl.⁵ .......................... A61B 5/00; A61N 1/05
[52] U.S. Cl. ................ 128/786; 128/419 P; 128/632; 128/642
[58] Field of Search ............ 128/786, 784, 785, 419 P, 128/642, 632, 635, 637, 675, 673, 783; 604/31, 66, 67; 606/1, 32, 129

[56] References Cited

U.S. PATENT DOCUMENTS

| | | | |
|---|---|---|---|
| 3,088,323 | 5/1963 | Welkowitz et al. | 128/675 |
| 4,176,659 | 12/1979 | Rolfe | 128/635 |
| 4,202,339 | 5/1980 | Wirtzfeld et al. | 128/419 PG |
| 4,282,885 | 8/1981 | Bisping | 128/785 |
| 4,311,153 | 1/1982 | Smits | 128/785 |
| 4,340,615 | 7/1982 | Goodwin et al. | 128/632 |
| 4,381,011 | 4/1983 | Somers, 3rd | 128/635 |
| 4,403,984 | 9/1983 | Ash et al. | 604/66 |
| 4,478,222 | 10/1984 | Koning et al. | 128/632 |
| 4,485,813 | 12/1984 | Anderson et al. | 128/675 |
| 4,543,955 | 10/1985 | Schroeppel | 604/66 |
| 4,716,887 | 1/1988 | Koning et al. | 128/419 PG |
| 4,951,687 | 8/1990 | Ufford et al. | 128/784 |
| 4,955,382 | 9/1990 | Franz et al. | 128/786 |
| 5,000,180 | 3/1991 | Kuypers et al. | 128/635 |
| 5,105,812 | 4/1992 | Corman | 128/635 |

FOREIGN PATENT DOCUMENTS

| | | | |
|---|---|---|---|
| 0158030 | 10/1985 | European Pat. Off. | 606/1 |
| 0336984 | 10/1989 | European Pat. Off. | 128/635 |
| 1544396 | 2/1990 | U.S.S.R. | 606/32 |
| 2135196 | 8/1984 | United Kingdom | 128/642 |

Primary Examiner—Kyle L. Howell
Assistant Examiner—Kennedy J. Schaetzle
Attorney, Agent, or Firm—John R. Merkling

[57] ABSTRACT

A lead system for a cardiac pacemaker comprising a lead having a proximal end and a distal end, the distal end having an electrode. A lumen passes through the lead from the proximal end to the distal end. A sensor-carrying flexible stylet is adapted to be inserted into the lumen of the lead. At the proximal end of the flexible stylet, there is an attachment means comprising a distal female connector and a proximal male connector adapted to connect to a pacemaker. The lead can also be provided with a distal aperture, which permits transport into the lead to the sensor of blood, gasses, heat, light, chemical or other phenomenon which are to be sensed.

19 Claims, 2 Drawing Sheets

PACER LEAD WITH REPLACEABLE SENSOR

FIELD OF MY INVENTION

My invention relates to leads for implantable therapeutic devices, and in particular to leads for implantable cardiac pacemakers. More specifically, my invention relates to leads for cardiac pacemakers having sensors for detecting physiological phenomena in the heart.

BACKGROUND OF MY INVENTION

Cardiac pacemakers stimulate the heart with electrical impulses to induce a heartbeat. Pacemakers may also sense the condition of the heart so that stimuli may be applied in an appropriate manner. Pacemakers have been developed which respond to detected physiological parameters to provide variable pacing rates which more nearly approximate the physiologic requirements of a patient. Such parameters as pH, oxygen saturation, intracardiac temperature and other parameters are sensed alone or in combination to provide information concerning the physiologic demands of the patient.

Cardiac pacing leads designed to sense such parameters, other than merely sensing electrical signals and pacing the heart, are typically of special design. For example, a pacemaker lead with a temperature sensor is disclosed in U.S. Pat. No. 4,726,383, which requires implantation of a specific lead containing a thermistor transducer. A specialized lead with a pressure sensor or an accelerometer is disclosed in U.S. Pat. No. 4,666,617 and again requires a specific lead with a built-in sensor. U.S. Pat. No. 4,690,143 discloses a pacemaker having a lead which can generate electrical power piezoelectrically from the movement of the lead. Such a lead requires a piezoelectric element built in along the length of the lead.

These designs require a specialized lead for sensing special parameters. Consequently, if a pacemaker responsive to such parameters is to be implanted into a patient, the lead must correspond to the given pacemaker. It is not unusual for patients to require or want replacement pacemakers, either because the batteries on their prior pacemaker are expended or to gain new and improved features. In such situations, a lead may already be implanted in the heart. Such a lead will have achieved a reliable fixation. Moreover, it is a known phenomenon for a newly implanted lead to have an initial period of increased impedance resulting, apparently, from inflammation or the response of the heart to a new foreign body in tissue. Leads that have stabilized in position can, therefore, be expected to have superior impedance characteristics. It may be impossible or risky to remove a lead because of fixation to heart tissue. A physician, therefore, may want to avoid removal of a lead which is already successfully implanted in the heart.

Moreover, specialized sensors such as pressure or accelerometer sensors tend to have a finite life and the sensors may fail over time. It is desirable, therefore, that the sensor should be replaceable, without replacing the entire lead.

It is also possible to combine pacing, antitachycardia, defibrillation, or other electrical therapy with a chemical or drug therapy. Both therapies may be delivered to the heart through a single lead.

With the foregoing in mind, it is an object of my invention to provide a lead system wherein different sensors can be selected for different applications.

It is also an object of my invention to provide a lead system wherein the sensor can be replaced without explanting the entire lead.

A further object of my invention is to provide apparatus whereby a sensor can be added to an existing, implanted lead without removing the lead from the patient's body.

Yet another object of my invention is to provide a lead which can deliver both electrical and chemical therapies to the heart of the patient.

SUMMARY OF MY INVENTION

I have invented a lead system for a cardiac pacemaker comprising a lead having a proximal end and a distal end, the distal end having an electrode. A lumen passes through the lead from the proximal end to the distal end. A sensor-carrying flexible stylet is adapted to be inserted into the lumen of the lead. At a distal end of the flexible stylet, there is a sensor. At the proximal end, there is an attachment means comprising a distal female connector and a proximal male connector adapted to connect to a pacemaker.

The lead of my invention can also be provided with a distal aperture, which permits transport into the lead to the sensor of blood gasses, heat, light, chemical or other phenomena which are to be sensed.

With leads having such an aperture, it is possible to inject drugs, marker materials or other substances into the heart through the lumen. Furthermore, substances may be inserted through the lumen to clean the aperture.

DETAILED DESCRIPTION OF MY PREFERRED EMBODIMENT

Figure 1:
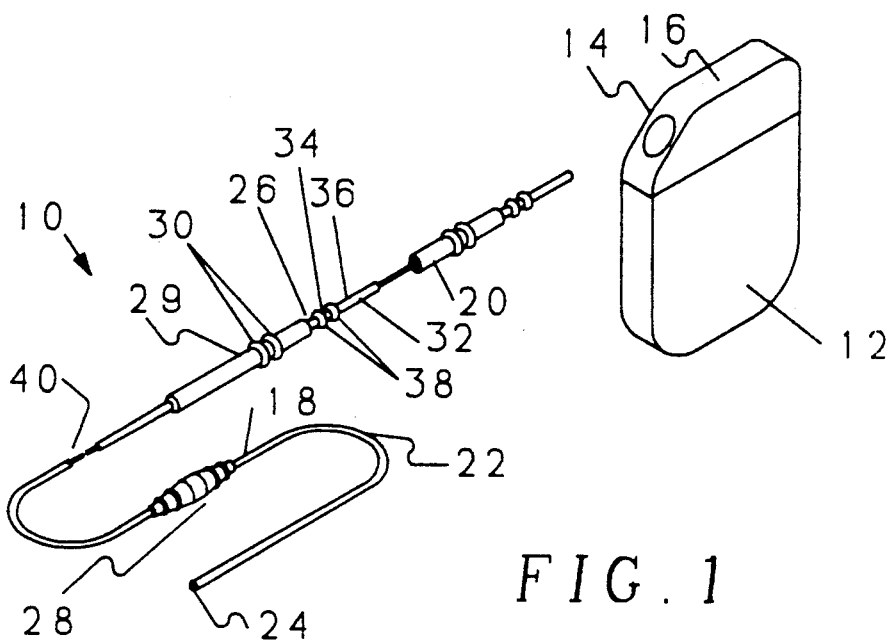
FIG. 1 is a perspective view of a lead system according to my present invention and cardiac pacemaker.

I will now describe my preferred embodiment of my invention. In referring to the accompanying figures, like numerals will be used to refer to like parts throughout this description. In FIG. 1 a lead system, generally designated 10, is shown in perspective view. A cardiac pacemaker 12 is shown, to which the lead system 10 may be attached by inserting the lead system into a socket 14 in a header 16.

The lead system 10, according to my present invention, comprises a lead 18 and a flexible, sensor bearing stylet 20. The lead 18 is preferably substantially conventional, unless it is desired to provide an aperture, as will be explained more fully below. Many available leads have at least one central lumen into which a stylet is conventionally inserted for manipulating the lead during insertion. The stylet 20 of my invention can be inserted into such leads to retrofit an already implanted lead or a new lead of a selected type with an additional sensor.

The lead comprises a flexible body 22 housing an internal conductor (not shown). The internal conductor connects at least one electrode 24, here shown at the distal tip of the lead, to a male connector 32 at a proximal end 26 of the lead. A suture ring 28 is provided for securing the point of insertion of the lead into a vein. In my preferred embodiment, the male connector 32 comprises an enlarged cylindrical body 29 carrying circumferential sealing rings 30. The male connector 32 has a plurality of electrical contacts 34, 36 insulated from one another by circumferential seals 38. A lumen 40 passes through the lead along its longitudinal axis from the proximal end to the distal end. As is conventional, a stiffening stylet can be inserted into this lumen to aid in the insertion of the lead. Means may also be provided on the lead for securing the electrode in a selected position within the heart. Such known means include outwardly extending tines or corkscrews.

Figure 2:
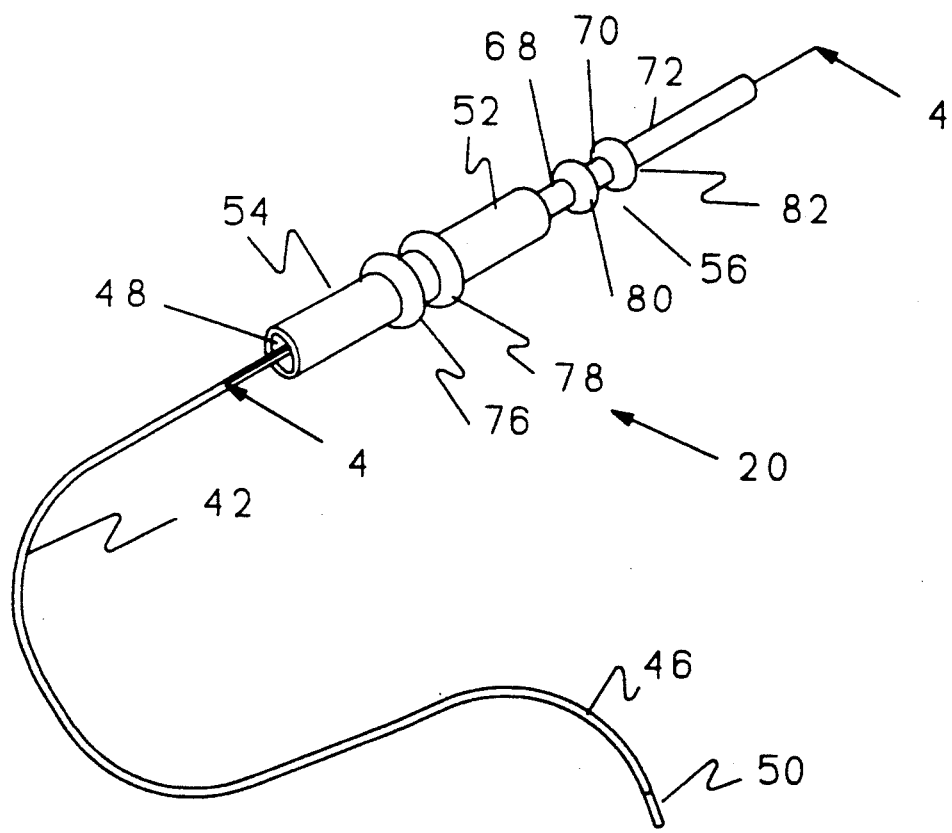
FIG. 2 is perspective view of a flexible, sensor-carrying stylet according to my present invention.
Figure 4:
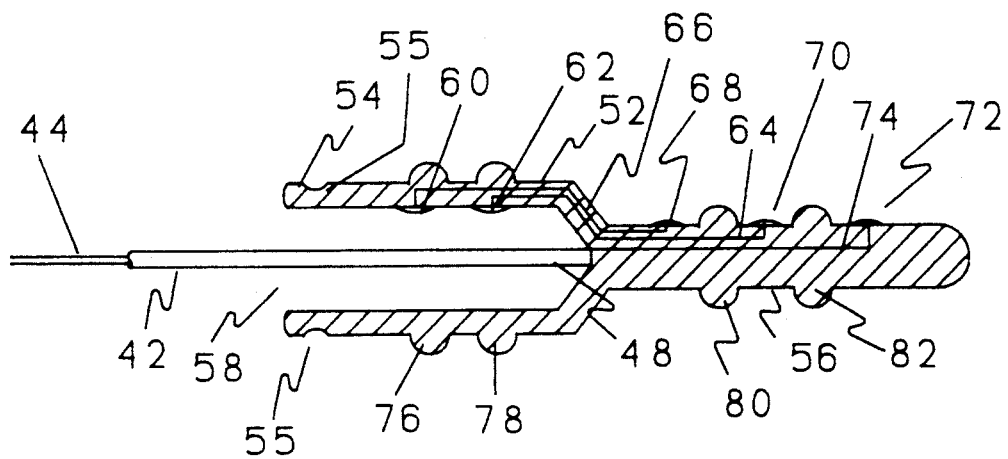
FIG. 4 is a through section of a proximal end of the flexible stylet of FIG. 2 taken along line 4—4.

The flexible stylet 20, illustrated in FIG. 2 and FIG. 4, comprises a flexible elongated body 42 having internal conductors 44 extending from a distal end 46 to a proximal end 48 thereof. At the distal end 46 there is a sensor 50. This may be any kind of sensor for a desired parameter, such as a pressure sensor, a temperature sensor, an accelerometer, or a piezoelectric element. Motion, vibration, acceleration, acoustical signals or temperature may be measured with an appropriate sensor. In this first embodiment of my invention, the parameter to be measured should be detectable through the lead 18.

An hermaphrodite connector 52 is attached to the elongated body 42 at its proximal end 48. The hermaphrodite connector 52 comprises a distal female connector 54 and a proximal male connector 56. The female connector 54 comprises an aperture 58 adapted to engage the proximal end of the lead 18 in substantially the same manner as the aperature 14 in the pacer 12 engages a conventional lead. A suture tied in a circumferential groove 55 will compress the female connector 54 and will hold the proximal end of the lead 18 and the connector together. Electrical contacts 60, 62 are provided for making electrical contact with the proximal end of the lead. The contacts 60, 62 are connected by conductors 64, 66 to electrical contacts 68, 70 which are adapted to connect to the pacer 12 through the aperture 14 in the header 16. Additional electrical contacts, such as contact 72, are provided and connected electrically through wires, such as 74, to the stylet 42 and then to the sensor 50. On the exterior of the female connector, circumferential seals 76, 78 are provided to prevent body fluids from entering the header 16 of the pacemaker 12 when the lead system 10 is connected to the pacer. The male connector is also provided with circumferential seals 80, 82 to aid in electrically separating electrical contacts such as contacts 68, 70 and 72.

To use the lead system 10 of my invention, a physician would insert the lead 18 through a vein into the heart in a conventional manner using a stiffening stylet. The stylet would then be withdrawn and the flexible stylet 20 would be inserted. The flexible stylet 42 would pass through the lumen 40 of the lead until the sensor 50 was lodged in the distal end of the lead. The female connector of the flexible stylet would be fitted over the male connector of the lead. The pacemaker 12 would then be attached to the male connector of the flexible stylet. It will be apparent that the flexible stylet with sensor can be utilized with any lead having at least one lumen of sufficient dimension to allow the stylet to be inserted into the lead. Therefore, the flexible stylet can be used either with a new lead, as illustrated in FIG. 1, or in conjunction with a lead already implanted in the body.

Figure 3:
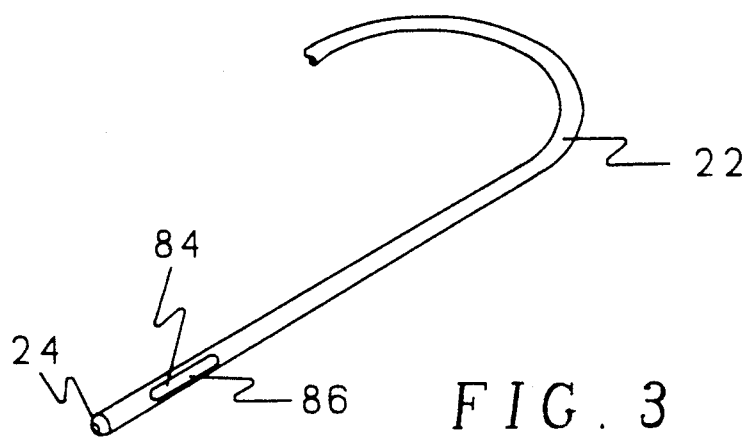
FIG. 3 is an enlarged view of a distal tip of a lead with an aperture.

It is possible, however, to also provide a specialized lead for use with the flexible, sensor-bearing stylet. Such a lead may have an aperture 84 in the distal end thereof as illustrated in FIG. 3. The aperture 84 permits transmission into the lead of blood gasses, heat, light or other physical or chemical phenomena which are to be sensed. Heat and other conditions may be transmitted more effectively to the sensor. An open aperture may be used or the aperture 84 may be covered by a permeable membrane 86 which would permit the transmission of certain components (for example, gas or bodily fluids or light,) while inhibiting other components. The aperture is designed not to degrade either the electrical or mechanical properties of the lead.

If an open aperture is used or an aperture with a reverse permeable membrane, drugs, marker materials or other substances may be inserted into the heart through the lumen of the lead using a long hollow stylet or directly through the lumen. Such substances may be used in the treatment of the patient or to clean the aperture by dissolving body substances which may have built up on it.

Figure 5:
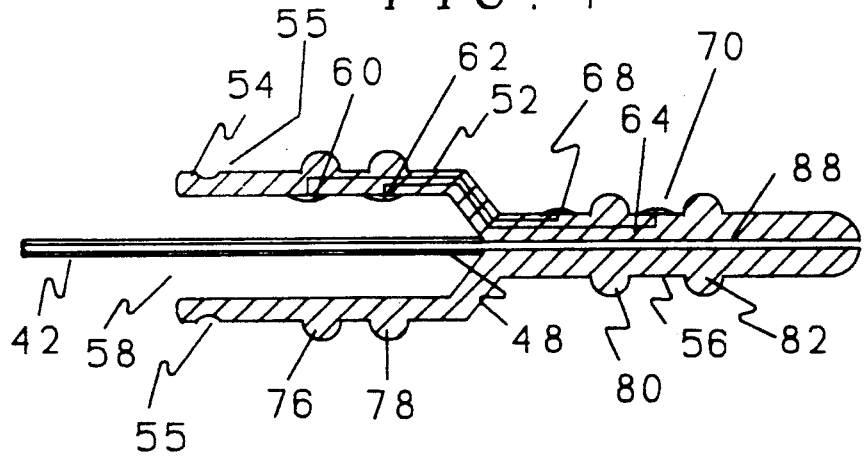
FIG. 5 is a through section, similar to FIG. 4, of an alternative embodiment of my invention with drug delivery capability.

An alternative embodiment of my invention is shown in FIG. 5. This embodiment is useful in delivering a drug therapy to the heart. Instead of the contact 72 and electrical wire 74, a lumen 88 passes through the stylet 42 and the connector 52. Using a pacemaker 12 provided with a drug supply and diffusion pump, a drug therapy can be administered through the lead. The stylet 42 is, in this embodiment, a catheter capable of transporting a therapeutic drug to a location within the heart.

It will be apparent to those skilled in the art that my invention can be embodied in other configurations without departing from the teachings or essential characteristics thereof. The foregoing description is, therefore, to be considered illustrative and not restrictive and the scope of my invention to be defined by the following claims. All changes or variations that would come within the meaning of equivalency of the claims are intended to be incorporated therein.

I claim as my invention:

1. A lead assembly for implantation in a patient, the assembly comprising:
    an electrode adapted for insertion into a chamber of the patient's heart for electrical stimulation thereof;
    a lead connected to a proximal end of said electrode and adapted to transmit electrical impulses between the electrode and a proximal end of the lead, the lead having a lumen extending through the lead from the proximal end to a distal end thereof;
    means at the proximal end of the lead capable of being used for connecting the lead to an implantable device;
    contact means at the proximal end of the lead for making an electrical connection to transmit said electrical impulses; and
    removable sensor means, said sensor means comprising
        a sensor adapted to pass through the lumen of said lead;

flexible stylet means electrically connected to said sensor at a distal end of said stylet means;

connector means electrically connected to said stylet means for engaging the lead connecting means and for making contact with said contact means; and means for mechanically and electrically attaching said removable sensor means to an implantable therapeutic device.

2. The lead assembly according to claim 1 wherein the lead connecting means comprise a male plug and a plurality of circumferential sealing rings and wherein the stylet connector means comprise a sleeve and an axially disposed female recess for receiving said male plug.

3. The lead assembly according to claim 2 wherein the stylet attaching means comprise a male plug.

4. The lead according to claim 1 wherein the lead further comprises an aperture at the distal end of said lead.

5. The lead assembly according to claim 4 wherein the lead connecting means comprise a male plug and a plurality of circumferential sealing rings and wherein the stylet connector means comprise a sleeve and an axially disposed female recess for receiving said male plug.

6. The lead assembly according to claim 5 wherein the stylet attaching means comprise a male plug.

7. The lead assembly according to claim 4 wherein the lead further comprises a permeable membrane covering said aperture.

8. The lead assembly according to claim 7 wherein the lead connecting means comprise a male plug and a plurality of circumferential sealing rings and wherein the stylet connector means comprise a sleeve and an axially disposed female recess for receiving said male plug.

9. The lead assembly according to claim 8 wherein the stylet attaching means comprise a male plug.

10. A removable sensor assembly for insertion into a lead in a patient, the lead having a lumen extending through the lead from a proximal end to a distal end thereof and having means at the proximal end of the lead capable of being used for connecting the lead to an implantable device, the assembly comprising:

a sensor adapted to pass through the lumen of said lead;

flexible stylet means electrically connected to said sensor at a distal end of said stylet means;

connector means electrically connected to said stylet means for engaging the lead connecting means; and means for mechanically and electrically attaching said removable sensor means to an implantable therapeutic device.

11. The lead assembly according to claim 10 wherein the stylet connector means comprise a sleeve and an axially disposed female recess for receiving lead connecting means comprising a male plug and a plurality of circumferential sealing rings.

12. The lead assembly according to claim 11 wherein the stylet attaching means comprise a male plug.

13. A lead assembly for implantation in a patient, the assembly comprising:

an electrode adapted for insertion into a chamber of the patient's heart for electrical stimulation thereof;

a lead connected to a proximal end of said electrode and adapted to transmit electrical impulses between the electrode and a proximal end of the lead, the lead having a lumen extending through the lead from the proximal end to a distal end thereof, said lead having an aperture at said distal end;

means at the proximal end of the lead capable of being used for connecting the lead to an implantable device;

contact means at the proximal end of the lead for making an electrical connection to transmit said electrical impulses; and removable catheter means, said catheter means comprising a catheter adapted to pass through the lumen of said lead from the proximal end to the distal end of said lead;

connector means electrically connected to said catheter for engaging the lead connecting means and for making contact with said contact means; and means for mechanically and electrically attaching said removable catheter means to an implantable therapeutic device.

14. The lead assembly according to claim 13 wherein the lead connecting means comprise a male plug and a plurality of circumferential sealing rings and wherein the catheter connector means comprise a sleeve and an axially disposed female recess for receiving said male plug.

15. The lead assembly according to claim 14 wherein the catheter attaching means comprise a male plug.

16. The lead assembly according to claim 15 wherein the lead further comprises a permeable membrane covering said aperture.

17. A removable catheter assembly for insertion into a lead in a patient, the lead having a lumen extending through the lead from a proximal end to a distal end thereof, having means at the proximal end of the lead capable of being used for connecting the lead to an implantable device, and having an aperture at the distal end thereof the assembly comprising:

a catheter adapted to pass through the lumen of said lead;

connector means electrically connected to said catheter for engaging the lead connecting means; and means for mechanically and electrically attaching said catheter to an implantable therapeutic device.

18. The catheter assembly according to claim 17 wherein the catheter connector means comprise a sleeve and an axially disposed female recess for receiving lead connecting means comprising a male plug and a plurality of circumferential sealing rings.

19. The lead assembly according to claim 18 wherein the catheter attaching means comprise a male plug.

* * * * *